United States Patent
Kang et al.

(10) Patent No.: US 9,955,948 B2
(45) Date of Patent: May 1, 2018

(54) CAPACITIVE MICROMACHINED ULTRASONIC TRANSDUCER PROBE USING WIRE-BONDING

(71) Applicant: SAMSUNG ELECTRONICS CO., LTD., Suwon-si (KR)

(72) Inventors: Sungchan Kang, Hwaseong-si (KR); Byunggil Jeong, Anyang-si (KR); Sangha Park, Seoul (KR); Hyungjae Shin, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 532 days.

(21) Appl. No.: 14/728,341

(22) Filed: Jun. 2, 2015

(65) Prior Publication Data
US 2016/0007959 A1    Jan. 14, 2016

(30) Foreign Application Priority Data

Jul. 9, 2014    (KR) ........................ 10-2014-0086155

(51) Int. Cl.
*A61B 8/00*    (2006.01)
*B06B 1/02*    (2006.01)

(52) U.S. Cl.
CPC .......... *A61B 8/4444* (2013.01); *B06B 1/0292* (2013.01); *A61B 2562/166* (2013.01);
(Continued)

(58) Field of Classification Search
CPC ............ A61B 8/4444; A61B 2562/166; H01L 2224/49433; H01L 2224/48091;
(Continued)

(56) References Cited

U.S. PATENT DOCUMENTS

| | | | |
|---|---|---|---|
| 7,427,825 B2 | 9/2008 | Frey et al. | |
| 7,687,976 B2 * | 3/2010 | Haider | A61B 1/0005 600/459 |

(Continued)

FOREIGN PATENT DOCUMENTS

| | | |
|---|---|---|
| JP | 4961224 B2 | 6/2012 |
| KR | 10-1330733 B1 | 11/2013 |

OTHER PUBLICATIONS

Communication dated Dec. 16, 2015, issued by the European Patent Office in counterpart European Patent Application No. 15175742.4.
(Continued)

*Primary Examiner* — Daniel Pihulic
(74) *Attorney, Agent, or Firm* — Sughrue Mion, PLLC

(57) ABSTRACT

Provided are capacitive micromachined ultrasonic transducer (CMUT) probes that use wire bonding. A CMUT probe includes a CMUT chip which includes a plurality of first electrode pads which are disposed on a first surface thereof, a printed circuit board (PCB) which is disposed on the first surface of the CMUT chip and which is configured to expose the plurality of first electrode pads, a plurality of second electrode pads which are disposed on the PCB and which correspond to respective ones of the plurality of first electrode pads, and a plurality of wires which connect each respective one of the plurality of first electrode pads to the corresponding one of the plurality of second electrode pads.

20 Claims, 4 Drawing Sheets

(52) U.S. Cl.
CPC ............... *H01L 2224/4824* (2013.01); *H01L 2224/48091* (2013.01); *H01L 2224/49433* (2013.01); *H01L 2924/00014* (2013.01)

(58) Field of Classification Search
CPC . H01L 2924/00014; H01L 2224/45015; H01L 2224/4824; H01L 2924/207; H01L 2224/45099; B06B 1/0292
See application file for complete search history.

(56) References Cited

U.S. PATENT DOCUMENTS

| | | | |
|---|---|---|---|
| 8,480,208 | B2 | 7/2013 | Takemoto et al. |
| 8,540,640 | B2 | 9/2013 | Sano et al. |
| 2002/0068426 | A1 | 6/2002 | Fjelstad et al. |
| 2006/0138626 | A1 | 6/2006 | Liew et al. |
| 2007/0194415 | A1 | 8/2007 | Seng et al. |
| 2008/0093748 | A1 | 4/2008 | Chen |
| 2008/0183078 | A1* | 7/2008 | Haider ............... A61B 1/0005 600/443 |
| 2008/0296717 | A1 | 12/2008 | Beroz et al. |
| 2010/0179430 | A1 | 7/2010 | Sano et al. |
| 2013/0032936 | A1 | 2/2013 | Formosa |
| 2016/0007959 | A1* | 1/2016 | Kang ............... A61B 8/4444 600/459 |

OTHER PUBLICATIONS

Alessandro Stuart Savoia et al; "A CMUT Probe for Medical Ultrasonography: From Microfabrication to System Integration"; IEEE Transactions on Ultrasonics, Ferroelecirics, and Frequency Control; vol. 59; No. 6, Jun. 2012; pp. 1127-1138.

* cited by examiner

CAPACITIVE MICROMACHINED ULTRASONIC TRANSDUCER PROBE USING WIRE-BONDING

CROSS-REFERENCE TO RELATED APPLICATION

This application claims priority from Korean Patent Application No. 10-2014-0086155, filed on Jul. 9, 2014, in the Korean Intellectual Property Office, the disclosure of which is incorporated herein by reference in its entirety.

BACKGROUND

1. Field

Exemplary embodiments relate to capacitive micromachined ultrasonic transducer probes using a wire-bonding in which a capacitive micromachined ultrasonic transducer chip and a printed circuit board are connected by a wire.

2. Description of the Related Art

A capacitive micromachined ultrasonic transducer (CMUT) is an apparatus that transforms an electrical signal to an ultrasonic signal or vice versa.

In order to manufacture an ultrasonic probe, a CMUT is bonded to an electrical circuit. The bonding may be performed by using a wire bonding method or a flip chip bonding method. When the flip chip bonding method is used to connect a CMUT to a printed circuit board (PCB), a bonding process may be complicated, and a manufacturing cost may be relatively high.

When the wire bonding method is used, an area required for wire bonding may be increased, and accordingly, an active area of the CMUT may be decreased in an ultrasonic probe. As a result, measuring quality may be decreased.

A size of an ultrasonic probe may be determined according to an object to be measured. For example, in the case of an ultrasonic probe for measuring the heart, the ultrasonic probe must be located between the ribs of a human body, and thus, the size of a short measuring unit of the ultrasonic probe may be determined to be below approximately 20 mm. Accordingly, an area of a CMUT chip to be mounted in the ultrasonic probe is limited. A magnitude of ultrasonic sound pressure and a focal distance of an ultrasonic probe both depend on an active area of a CMUT chip, and thus, it is useful to maximize the active area of the CMUT chip.

SUMMARY

Provided are capacitive micromachined ultrasonic transducer modules in which an active area of a CMUT chip is increased by wire bonding the CMUT chip and a printed circuit board via an installing process with respect to the printed circuit board by which an electrode pad of the CMUT chip is exposed.

Additional aspects will be set forth in part in the description which follows and, in part, will be apparent from the description, or may be learned by practice of the presented exemplary embodiments.

According to one or more exemplary embodiments, a capacitive micromachined ultrasonic transducer (CMUT) probe includes: a CMUT chip which includes a plurality of first electrode pads which are disposed on a first surface thereof; a printed circuit board (PCB) which is disposed on the first surface of the CMUT chip and which is configured to expose the plurality of first electrode pads; a plurality of second electrode pads which are disposed on the PCB and which correspond to respective ones of the plurality of first electrode pads; and a plurality of wires which connect each respective one of the plurality of first electrode pads to the corresponding one of the plurality of second electrode pads.

The CMUT chip may include a plurality of channels disposed in a row in a first direction, each of plurality of the channels including at least two third electrode pads that are disposed at predetermined gaps in a second direction which is perpendicular to the first direction, and the at least two third electrode pads of each of the plurality of channels being disposed at predetermined gaps in the second direction.

The CMUT probe may further include a plurality of first connection wires which connect each respective one of the plurality of first electrode pads to a corresponding one of the plurality of third electrode pads.

Each of the plurality of channels may further include a second connection wire which connects the corresponding at least two third electrode pads in the second direction.

Each of the plurality of channels may include a respective one of the plurality of first electrode pads and a respective one of the plurality of first connection wires, each of which is disposed on only one side thereof.

For each of the plurality of channels, the respective one of the plurality of first electrode pads may be disposed on a first side of the CMUT chip, and the respective one of the plurality of first connection wires may be disposed on a second side of the CMUT chip, wherein the first side of the CMUT chip faces the second side of the CMUT chip.

The plurality of first electrode pads may be disposed in two rows in a zigzag shape on both of a first side of the CMUT chip and a second side of the CMUT chip, wherein the first side of the CMUT chip faces the second side of the CMUT chip.

An area of each respective one of the plurality of first electrode pads may be larger than an area of each corresponding one of the plurality of second electrode pads.

A size of the PCB may be smaller than a size of the CMUT chip.

The CMUT probe may further include: an acoustic lens which includes a convex component which covers a front surface and at least a portion of a side surface of the CMUT chip and which contacts a measuring object; and a casing which covers a side of the acoustic lens and which exposes the convex component of the acoustic lens.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
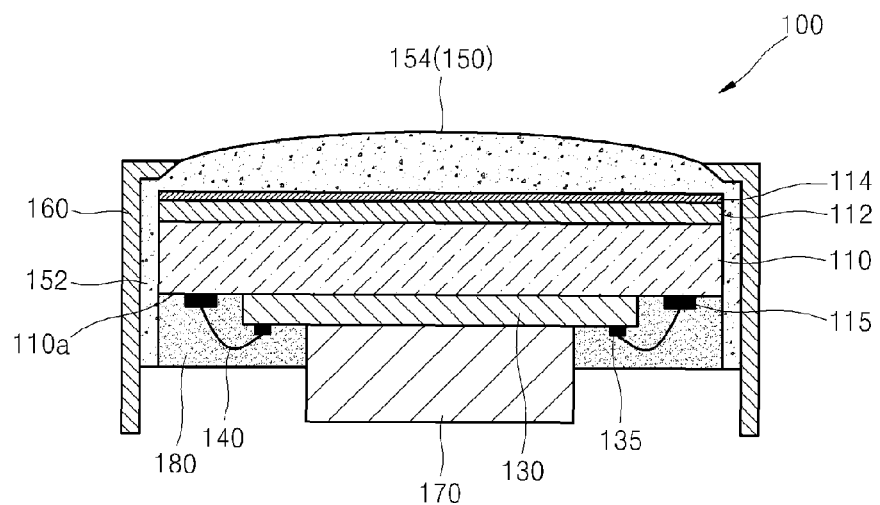
FIG. 1 is a schematic cross-sectional view of a CMUT probe, according to one or more exemplary embodiments.

Reference will now be made in detail to exemplary embodiments, examples of which are illustrated in the accompanying drawings. In the drawings, the thicknesses of layers and regions are exaggerated for clarity. The present inventive concept may, however, be embodied in many different forms, and should not construed as limited to the exemplary embodiments set forth herein. It will also be understood that when an element is referred to as being "above' or "on" another element, it can be directly on the other element, or intervening layers may also be present. Like reference numerals in the drawings denote like elements throughout the specification, and thus their description will be omitted.

FIG. 1 is a schematic cross-sectional view of the structure of a capacitive micromachined ultrasonic transducer (CMUT) probe 100, according to one or more exemplary embodiments.

Referring to FIG. 1, the CMUT probe 100 includes a CMUT chip 110 and a printed circuit board (PCB) 130. The CMUT chip 110 includes first electrode pads 115 for electrically connecting to each of the elements on a first surface 110a of the CMUT chip 110, which is opposite to an active surface of the CMUT chip 110 on which a membrane 112 is formed. The PCB 130 is disposed on the first surface 110a of the CMUT chip 110. The PCB 130 may be adhered to the CMUT chip 110 by using an adhesive, such as epoxy. The membrane 112 and an upper electrode 114, which is a common electrode, may be stacked sequentially upon the active surface of the CMUT chip 110.

Figure 2:
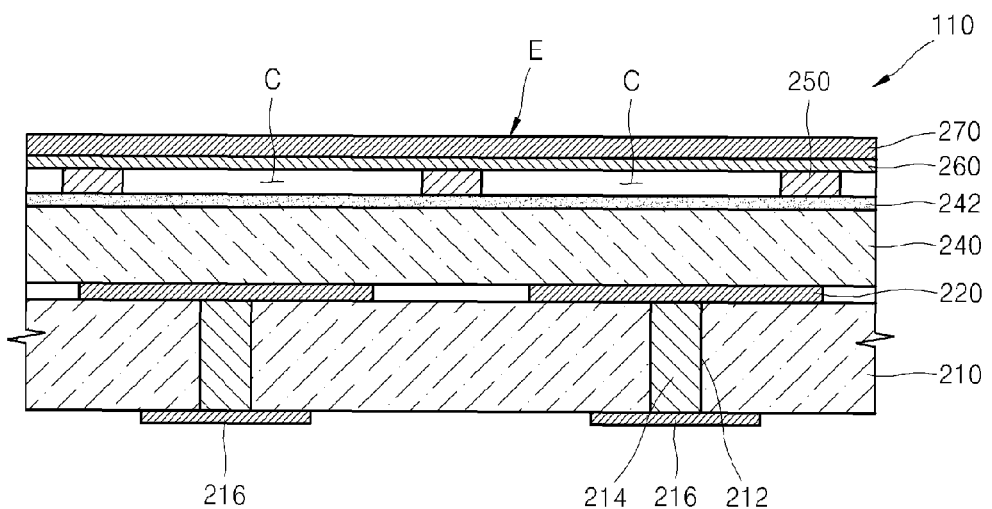
FIG. 2 is a cross-sectional view of the CMUT chip of FIG. 1, according to one or more exemplary embodiments.

FIG. 2 is a cross-sectional view of the CMUT chip 110 of FIG. 1, according to one or more exemplary embodiments.

Referring to FIG. 2, the CMUT chip 110 may include a through-silicon via (TSV) substrate 210 and a device substrate 240 that is bonded to the TSV substrate 210. The TSV substrate 210 and the device substrate 240 may be bonded by a eutectic bond.

The TSV substrate 210 may be formed of silicon and may have a plurality of through-holes 212 therethrough. The CMUT chip 110 includes a plurality of elements E. Each through-hole 212 may be formed in the TSV substrate 210 to correspond to each element E. An insulation layer (not shown) may be formed on the through-holes 212 and a surface of the TSV substrate 210.

The device substrate 240 may be formed of a conductive material having a thickness of a few tens of micrometers. The device substrate 240 may have a thickness in which falls within a range from about 10 µm to about 50 µm. The device substrate 240 may be formed of low resistance silicon that is highly doped with impurities. The device substrate 240 may be used as a lower electrode.

The device substrate 240 may adjoin an insulation layer 242 which is disposed thereon, a supporting unit 250 which forms cavities C, and a membrane 260 that covers the cavities C on the supporting unit 250. An upper electrode 270 may be formed on the membrane 260. The membrane 260 may be formed of silicon. The supporting unit 250 may be formed of an insulating material. The supporting unit 250 may include an oxide or a nitride. For example, the supporting unit 250 may be formed of silicon oxide.

In FIG. 2, the insulation layer 242 is formed on an upper surface of the device substrate 240. However, the current exemplary embodiment is not limited thereto. For example, the insulation layer 242 may be formed between the membrane 260 and the supporting unit 250.

The upper electrode 270 may include any one or more of gold (Au), copper (Cu), tin (Sn), silver (Ag), aluminum (Al), platinum (Pt), titanium (Ti), nickel (Ni), chromium (Cr), or a mixture of these materials.

The insulation layer 242 may include an oxide or a nitride. For example, the insulation layer 242 may be formed of silicon nitride.

In FIG. 2, two cavities C are formed in one element E. However, the current exemplary embodiment is not limited thereto, and a single cavity C or a plurality of cavities C may be formed in a single element E.

Bonding pads 220 that are respectively connected to via metals 214 in the through-holes 212 may be formed on a lower surface of the device substrate 240. The bonding pads 220 may be formed of eutectic metal, such as, for example, an Au—Sn eutectic material.

Third electrode pads 216 that are respectively connected to the via metals 214 are formed on a lower surface of the TSV substrate 210. A driving signal voltage may be applied to the third bonding pads 216. A ground voltage may be applied to the upper electrode 270.

Referring to FIG. 1, the PCB 130 is disposed on a first surface of the CMUT chip 110 so as to expose the first electrode pads 115. In particular, an area of the CMUT chip 110 is greater than that of the PCB 130. Second electrode pads 135 which respectively correspond to the first electrode pads 115 are formed on a lower surface of the PCB 130. The second electrode pads 135 are wire-bonded to the first electrode pads 115. The wire bonding may start from the second electrode pads 135 and proceed therefrom to the first electrode pads 115. Thus, the wires 140 connecting the first electrode pads 115 and the second electrode pads 135 are positioned within an area of the first surface 110a of the CMUT chip 110 and do not protrude outside the area of the CMUT chip 110. The second electrode pads 135 may be formed on a smaller area than that of the first electrode pads 115.

An acoustic lens 150 may be disposed on the upper electrode 114 of the CMUT chip 110. The acoustic lens 150 may be formed of silicon rubber. A protection member 152 which extends from the acoustic lens 150 may be formed to surround side surfaces of the CMUT chip 110. A casing 160 that exposes a convex component 154 of the acoustic lens 150 may be formed on the acoustic lens 150. The casing 160 may be formed of plastic.

A heat dissipation member 170 may be formed on the PCB 130 and disposed so as to face the acoustic lens 150. The heat dissipation member 170 may be formed of a metal having a high conductivity, such as, for example, aluminum.

A packing member 180 that covers and protects wires 140 may be formed on the first surface 110a of the CMUT chip 110 and the lower surface of the PCB 130 between the protection member 152 and the heat dissipation member 170. The packing member 180 may be formed of epoxy.

The convex component 154 may be convexly formed with a predetermined curvature from a side of the CMUT probe 100. The convex component 154 may have a length that is nearly equal to a corresponding length of the CMUT chip 110. An outer circumference of the CMUT chip 110 is formed to contact an inner circumference of the protection member 152. In particular, because the CMUT chip 110 is formed to fill the inner area of the CMUT probe 100, an active area of the CMUT chip 110 is relatively large as compared with a conventional CMUT chip which uses wire bonding.

Figure 3:
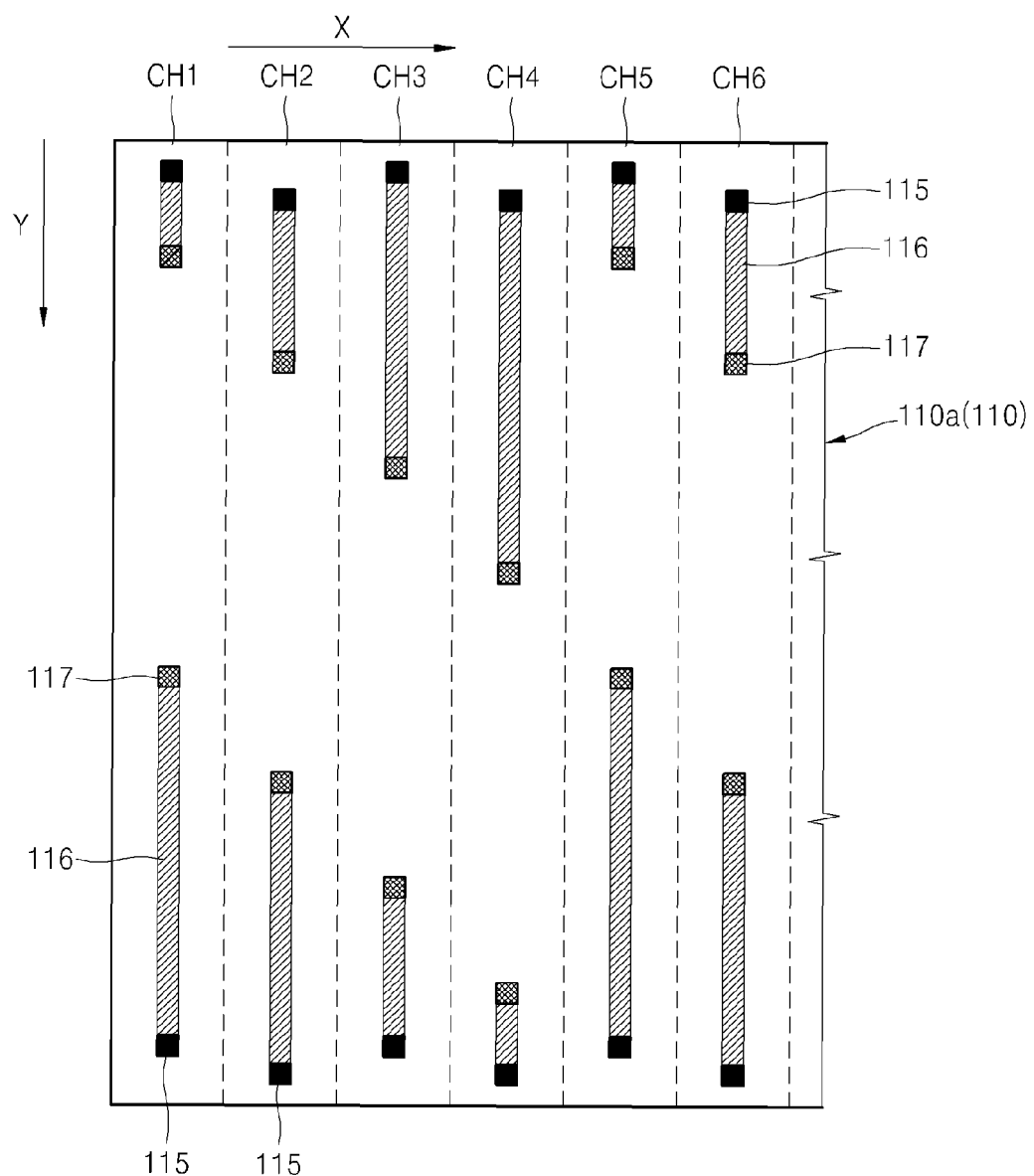
FIG. 3 is a plan view of the CMUT chip of FIG. 1, according to one or more exemplary embodiments.

FIG. 3 is a plan view of the CMUT chip 110 of FIG. 1, according to one or more exemplary embodiments. Like reference numerals are used to indicate elements that are substantially the same elements of FIGS. 1 and 2, and the descriptions thereof are omitted.

Referring to FIG. 3, a plurality of third electrode pads 117 are formed on the first surface 110a of the CMUT chip 110. The CMUT chip 110 may include a plurality of channels, for example, 80 to 128 channels. The plurality of channels may be one dimensionally disposed. Hereinafter, a CMUT chip 110 having 80 channels will be described.

The 80 channels may be sequentially formed in a first direction (as indicated by an arrow X). In FIG. 3, for convenience of description, 6 channels CH1 through CH6 are depicted. An element may be formed in each channel. Each channel may include one third electrode pad 117 or a plural number of third electrode pads 117 for power supply. In FIG. 3, each channel includes two third electrode pads 117. The plural number, for example, two or three third electrode pads 117 in each channel, may supply power notwithstanding an electrical failure in one of the third electrode pads 117 via the other third electrode pads 117. The third electrode pads 117 correspond to the third electrode pads 216 in FIG. 2.

As depicted in FIG. 3, the plural number of third electrode pads 117 in a single channel are uniformly separated (i.e., separated by equal distances) in a second direction (as indicated by an arrow Y), which may be perpendicular to the first direction, in order to secure spaces between the adjacent channels. For example, the third electrode pads 117 of four adjacent channels may be uniformly separated in the first and second directions, and this arrangement may be repeated.

Each of the third electrode pads 117 may extend towards a corresponding edge of the CMUT chip 110 to be connected to the first electrode pad 115. The third electrode pad 117 and the first electrode pad 115 may be connected via a first connection wire 116. The first connection wire 116 may be formed parallel to the second direction Y.

The first electrode pads 115 may be disposed in two rows in a zigzag shape. When the first electrode pads 115 are disposed in one row, there may be a short circuit between the adjacent first electrode pads 115.

At least one electrode pad (not shown) that is separated from the third electrode pads 117 may be formed to apply a ground voltage to the upper electrode 114 of the CMUT chip 110.

Figure 4:
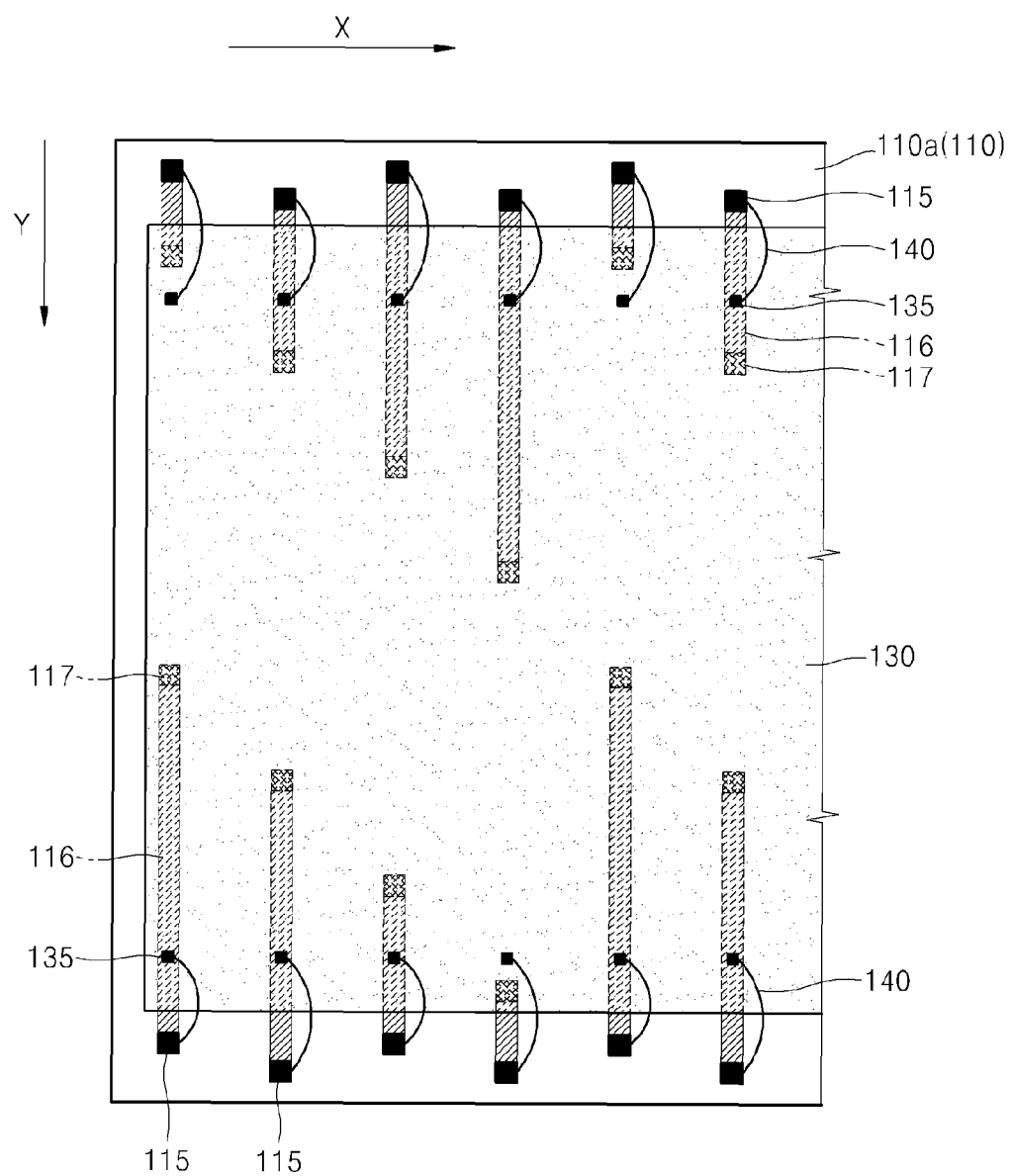
FIG. 4 is a portion of the plan view of a structure in which the CMUT chip of FIG. 1 and a printed circuit board are bonded together, according to one or more exemplary embodiments.

FIG. 4 is a portion of the plan view of a structure in which the CMUT chip 110 and the PCB 130 of FIG. 1 are bonded together, according to one or more exemplary embodiments. Like reference numerals are used to indicate elements that are substantially identical to the elements of FIGS. 1, 2, and 3, and thus the detailed descriptions thereof will not be repeated.

Referring to FIG. 4, the PCB 130 is bonded to the first surface 110a of the CMUT chip 110. The PCB 130 has a smaller surface than that of the CMUT chip 110, and the first electrode pads 115 of the CMUT chip 110 are exposed by the PCB 130. The second electrode pads 135 which respectively correspond to the first electrode pads 115 are formed on the PCB 130. The second electrode pads 135 may be disposed in a row, since the second electrode pads 135 are relatively smaller than the first electrode pads 115, but the current exemplary embodiment is not limited thereto. In particular, the first electrode pads 115 and the second electrode pads 135 may be disposed in various ways. For example, the second electrode pads 135 may also be disposed in two rows in a zigzag shape to correspond to the first electrode pads 115.

The second electrode pads 135 and the first electrode pads 115 are connected to each other by the wires 140. As shown in FIG. 4, the wires 140 are positioned within an area of the first surface 110a of the CMUT chip 110 and do not protrude outside the area of the CMUT chip 110. When using wire bonding, wires may be connected from the second electrode pads 135 to the first electrode pads 115, and thus, the second electrode pads 135 may have a smaller size than that of the first electrode pads 115.

In the CMUT probe 100 according to one or more exemplary embodiments, an electrical connection between the CMUT chip 110 and the PCB 130 is implemented on a rear surface of the CMUT chip 110. At this point, an active region of the CMUT chip 110 is electrically connected via wire bonding while occupying almost all inner area of the casing 160. Thus, an active area of the CMUT chip 110 is very large, and the measurement quality of the CMUT probe 100 may be increased.

Figure 5:
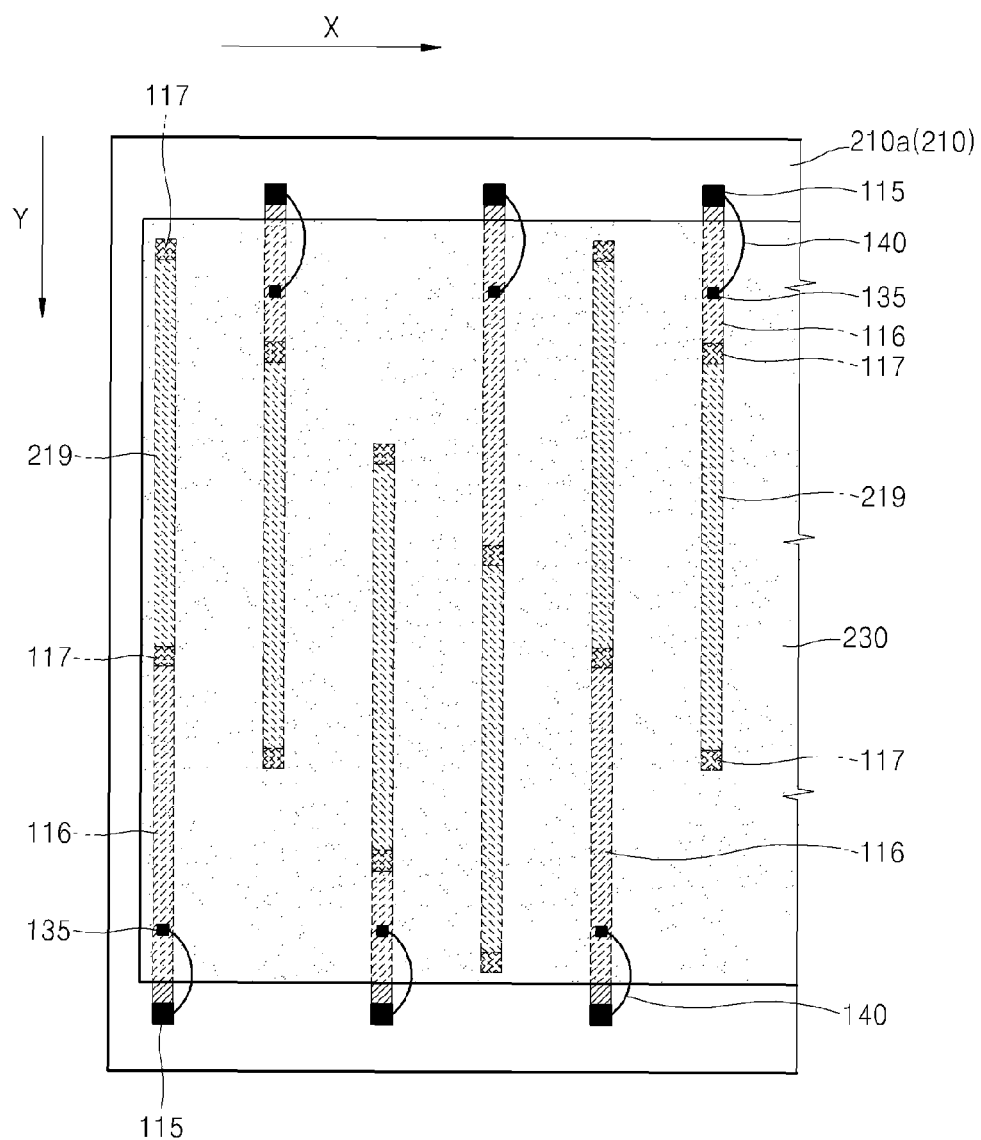
FIG. 5 is a portion of the plan view of a structure in which the CMUT chip and a printed circuit board are bonded together, according to one or more exemplary embodiments.

FIG. 5 is a portion of the plan view of a structure in which a CMUT chip 210 and a PCB 230 are connected together, according to one or more exemplary embodiments. Like reference numerals are used to indicate elements that are substantially identical to the elements of FIGS. 1, 2, 3, and 4, and thus the detailed descriptions thereof will not be repeated.

Referring to FIG. 5, the third electrode pads 117 of each of the channels are electrically connected via second connection wires 219 on a first surface 210a of the CMUT chip 210. The second connection wires 219 may be formed together with the third electrode pads 117 and the first connection wires 116 by patterning a metal layer. In each of the channel regions, only one first electrode pad 115 may be formed on one of both facing sides of the PCB 230, and also, the second electrode pads 135 may be formed adjacent to their corresponding first electrode pads 115. Further, as shown in FIG. 5, respective ones of the first electrode pads 115 and the first connection wires 116 may be alternatingly formed on both sides of the CMUT chip 210. The first electrode pads 115 corresponding to the second electrode pads 135 may be electrically connected via the wires 140.

In the CMUT chip 210 and the PCB 230 of FIG. 5, the numbers of first electrode pads 115, second electrode pads 135, and wires 140 therebetween are reduced to a half, as compared to the corresponding numbers thereof with respect to the CMUT chip 110 and the PCB 130 of FIG. 4, and thus, the wiring design may be easier than that of the CMUT chip 110 and the PCB 130 of FIG. 4.

However, the current exemplary embodiment is not limited thereto. For example, second connection wires 219 that connect the third electrode pads 117 of each channel may be further included in FIG. 4.

In a CMUT probe that uses wire bonding according to one or more exemplary embodiments, an electrical connection between a CMUT chip and a PCB is achieved on a rear surface of the CMUT chip. Thus, an active region of the CMUT chip occupies most of all the inner area of a casing, and accordingly, an active area of the CMUT chip is increased. Accordingly, the measuring quality of the CMUT probe may be increased.

In addition, the CMUT chip and the PCB are electrically connected to one another via wire bonding, and thus, a manufacturing process is relatively simple.

While exemplary embodiments have been described with reference to the figures, it will be understood by those of ordinary skill in the art that various changes in form and details may be made therein without departing from the spirit and scope of the present inventive concept, as defined by the following claims.

What is claimed is:

1. A capacitive micromachined ultrasonic transducer (CMUT) probe comprising:
    a CMUT chip which comprises a plurality of first electrode pads which are disposed on a first surface thereof;
    a printed circuit board (PCB) which is disposed on the first surface of the CMUT chip and which is configured to expose the plurality of first electrode pads;
    a plurality of second electrode pads which are disposed on the PCB and which correspond to respective ones of the plurality of first electrode pads; and
    a plurality of wires which connect each respective one of the plurality of first electrode pads to the corresponding one of the plurality of second electrode pads.

2. The CMUT probe of claim 1, wherein the CMUT chip comprises a plurality of channels disposed in a row in a first direction, each of the plurality of channels comprising at least two third electrode pads that are disposed at predetermined gaps in a second direction which is perpendicular to the first direction, and the at least two third electrode pads of each of the plurality of channels being disposed at predetermined gaps in the second direction.

3. The CMUT probe of claim 2, further comprising a plurality of first connection wires which connect each respective one of the plurality of first electrode pads to a corresponding one of the plurality of third electrode pads.

4. The CMUT probe of claim 2, wherein each of the plurality of channels further comprises a second connection wire which connects the corresponding at least two third electrode pads in the second direction.

5. The CMUT probe of claim 4, wherein each of the plurality of channels comprises a respective one of the plurality of first electrode pads and a respective one of the plurality of first connection wires, each of which is disposed on only one side thereof.

6. The CMUT probe of claim 5, wherein for each of the plurality of channels, the respective one of the plurality of first electrode pads is disposed on a first side of the CMUT chip, and the respective one of the plurality of first connection wires is disposed on a second side of the CMUT chip, wherein the first side of the CMUT chip faces the second side of the CMUT chip.

7. The CMUT probe of claim 1, wherein the plurality of first electrode pads are disposed in two rows in a zigzag shape on both of a first side of the CMUT chip and a second side of the CMUT chip, wherein the first side of the CMUT chip faces the second side of the CMUT chip.

8. The CMUT probe of claim 1, wherein an area of each respective one of the plurality of first electrode pads is larger than an area of each corresponding one of the plurality of second electrode pads.

9. The CMUT probe of claim 1, wherein a size of the PCB is smaller than a size of the CMUT chip.

10. The CMUT probe of claim 1, further comprising:
    an acoustic lens which includes a convex component which covers a front surface and at least a portion of a side surface of the CMUT chip and which contacts a measuring object; and
    a casing which covers a side of the acoustic lens and which exposes the convex component of the acoustic lens.

11. An ultrasonic transducer probe comprising:
    an ultrasonic transducer chip having an area and including first electrode pads;
    a printed circuit board (PCB) including second electrode pads;
    wires connecting the first electrode pads to the second electrode pads and being positioned within the area of the ultrasonic transducer chip and not protruding outside the area of the ultrasonic transducer chip.

12. The ultrasonic transducer probe of claim 11, wherein the ultrasonic transducer chip comprises channels disposed in a row in a first direction, each of the channels comprising at least two third electrode pads that are disposed at predetermined gaps in a second direction which is perpendicular to the first direction, and the at least two third electrode pads of each of the channels being disposed at predetermined gaps in the second direction.

13. The ultrasonic transducer probe of claim 12, further comprising first connection wires which connect each respective one of the first electrode pads to a corresponding one of the at least two third electrode pads.

14. The ultrasonic transducer probe of claim 12, wherein each of the channels further comprises a second connection wire which connects the corresponding at least two third electrode pads in the second direction.

15. The ultrasonic transducer probe of claim 14, wherein each of the channels comprises a respective one of the first electrode pads and a respective one of the first connection wires, each of which is disposed on only one side thereof.

16. The ultrasonic transducer probe of claim 15, wherein for each of the channels, the respective one of the first electrode pads is disposed on a first side of the ultrasonic transducer chip, and the respective one of the first connection wires is disposed on a second side of the ultrasonic transducer chip, wherein the first side of the ultrasonic transducer chip faces the second side of the ultrasonic transducer chip.

17. The ultrasonic transducer probe of claim 11, wherein the first electrode pads are disposed in two rows in a zigzag shape on both of a first side of the ultrasonic transducer chip and a second side of the ultrasonic transducer chip, wherein the first side of the ultrasonic transducer chip faces the second side of the ultrasonic transducer chip.

18. The ultrasonic transducer probe of claim 11, wherein an area of each respective one of the first electrode pads is larger than an area of each corresponding one of the second electrode pads.

19. The ultrasonic transducer probe of claim 11, wherein a size of the PCB is smaller than a size of the ultrasonic transducer chip.

20. The ultrasonic transducer probe of claim 11, further comprising:
    an acoustic lens which includes a convex component which covers a front surface and at least a portion of a side surface of the ultrasonic transducer chip and which contacts a measuring object; and
    a casing which covers a side of the acoustic lens and which exposes the convex component of the acoustic lens.

* * * * *